United States Patent [19]

Hüschelrath

[11] Patent Number: 4,821,204
[45] Date of Patent: Apr. 11, 1989

[54] METHOD AND DEVICE FOR TESTING FOR FLAWS WITH THE EDDY-CURRENT PRINCIPLE

[75] Inventor: Gerhard Hüschelrath, Laufach--Frohnhofen, Fed. Rep. of Germany

[73] Assignee: Nukem GmbH, Hanau, Fed. Rep. of Germany

[21] Appl. No.: 934,104

[22] Filed: Nov. 24, 1986

[30] Foreign Application Priority Data

Nov. 28, 1985 [DE] Fed. Rep. of Germany ....... 3542159

[51] Int. Cl.⁴ ...................... G06F 15/20; G01N 27/82
[52] U.S. Cl. ........................................ 364/481; 73/779; 324/209; 324/237; 324/240; 364/507; 364/552
[58] Field of Search ............... 364/481, 507, 508, 513, 364/550, 552, 571; 324/209, 216, 227, 228, 237, 238, 240, 259, 233; 73/760, 779

[56] References Cited

U.S. PATENT DOCUMENTS

| | | | |
|---|---|---|---|
| 4,193,028 | 3/1980 | Downs, II | 324/237 |
| 4,230,987 | 10/1980 | Mordwinkin | 324/233 |
| 4,322,683 | 3/1982 | Vieira et al. | 324/240 |
| 4,507,610 | 3/1985 | Nakaoka | 324/237 |
| 4,596,150 | 6/1986 | Kuhr | 73/779 |
| 4,628,261 | 12/1986 | Huschelrath et al. | 324/240 |
| 4,631,688 | 12/1986 | Boehm et al. | 324/233 |
| 4,641,092 | 2/1987 | Sakamoto et al. | 324/237 |
| 4,648,041 | 3/1987 | Tarr | 364/481 |
| 4,652,822 | 3/1987 | Wallace | 324/240 |

Primary Examiner—Parshotam S. Lall
Assistant Examiner—Kevin J. Teska
Attorney, Agent, or Firm—Cushman, Darby & Cushman

[57] ABSTRACT

The object of the invention is a method and a device for materials testing using the eddy-current principle. If a coil (30) is moved in relation to test specimens, magnetic alternating fields with differing frequencies are generated, these fields induce eddy-currents that cause a secondary field in the coil (30). A number of test specimens having the same structure and the same dimensions are measured. The measured values are stored. The coordinates of the center of gravity of the measured values in the complex plane are then determined. The phase angle is determined of that axis which runs longitudinally through the field (20) formed by the measured values in the complex plane. The center of gravity is then rotated into the origin of the coordinate system and the axis into a coordinate axis. Then a threshold value envelope determining a fault boundary is placed around the field of the measured values. The threshold value curve is then displaced by the coordinates of the center of gravity and rotated by the phase angle of the axis. In later measurement of test specimens for fault detection, the measured values are directly compared with the values of the transformed threshold value envelope.

13 Claims, 3 Drawing Sheets

METHOD AND DEVICE FOR TESTING FOR FLAWS WITH THE EDDY-CURRENT PRINCIPLE

BACKGROUND OF THE INVENTION

1. Field of the Art

The present invention relates to a method and a device for testing materials for flaws with the eddy-current principle.

2. Background of the Related Art

A method is known in which a coil moved in relation to the test specimen generates magnetic alternating fields which may or may not have different frequencies. These fields induce eddy-currents in the respective test specimen which cause a secondary field in the coil or in a separate sensing coil, the measured values of this secondary field being split into real and imaginary parts.

Also known is a device having a coil which moves in relation to test specimens, whereby magnetic alternating fields are generated which induce eddy-current in the respective test specimen, the currents causing a secondary field in the coil or in a sensing coil. The coil or sensing coil is connected to an evaluation unit comprising a unit for splitting the measured values into their real and imaginary parts, analog-digital converters connected to a bus, a computer, a memory, and comparators.

In non-destructive materials testing using eddy-currents, faults are detected from small changes in a relatively large signal. These minor changes can be measured using the bridge measuring method. In this method, a bridge circuit is provided in the test coil or in the instrument eddy-current testing instrument. The measuring operation is as follows: first, the bridge circuit is automatically or manually adjusted. The phase position of the measurement signal is rotated in an axis of the complex plane in order to eliminate disturbance signals present in the measurement signal. A separation of this type is possible if the disturbance signals have a different phase position than the fault signals. That part of the measurement signal falling to the axis, the so-called evaluation axis, is then compared with a sorting threshold only effective for this axis or a sector of the axis. If the signal portion exceeds the sorting threshold, then a fault is present and is signalled or recorded.

In analog-type eddy-current test instruments, there are narrow limits with regard to fault resolution and interference suppression. With digital eddy-current test instruments it is possible to achieve better fault resolution and interference suppression values. However, this involves more circuitry. In addition, digital instruments generally process the signals more slowly than do analog instruments.

In one digital device for materials testing with the eddy-current principle where various test frequencies are used, compensation values are generated at the various frequencies as a function of the initial size of the coil, the compensation values being typical for the disturbances. These compensation values are then superimposed on the initial values to eliminate the effect of the disturbances on the measurement.

In another known digital device for testing materials using the eddy-current principle, the complex measured values occurring during a test cycle are first checked as to whether only disturbance signals, disturbance signals in conjunction with fault signals, or only fault signals are present. If only fault signals are present, the measured values are directly processed. If disturbance signals in conjunction with faults signals are present, the disturbance signals are eliminated first before the fault signals are further processed for fault depth determination.

SUMMARY OF THE INVENTION

The object underlying the invention is a method for more rapid processing and evaluation of measurement signals. This object is achieved using a particular type of digital signal processing.

The present invention provides a method and an apparatus for testing materials for flaws with the eddy-current principle by moving a coil relative to test specimens to generate magnetic alternating fields in the test specimen with one or more frequencies. The fields induce eddy-currents in the respective test specimen which generate in the coil or in a sensing coil a secondary field producing electrical measuring values in response thereto. The measuring values are represented as digital complex numbers on a complex plane and are split into real and imaginary parts. In a first operating mode a number of fault-free test specimens of equal structure and equal dimensions are measured. The obtained measured values are stored by their real and imaginary parts in memory. A computer calculates the coordinates of a center of gravity of an area including the digital complex numbers. The computer calculates a phase angle between an axis of the complex plane and an axis which extends longitudinally across the area. The area is then displaced to an origin of the complex plane by the coordinates of the center of gravity. Also the axis which extends longitudinally across the area is rotated to the axis of the complex plane. Then a threshold value envelope enclosing the area, such as a rectangle, is generated. Thereafter, the threshold value envelope is displaced by the coordinates of the center of gravity and rotated by the phase angle. The transformed values of the threshold envelope are stored in a threshold value memory. In a second operating mode test specimens for detecting flaws are measured and the measured values are compared with the stored threshold values.

In the method according to the invention, measured values obtained during the measurement of possibly faulty test specimens are directly compared with the stored threshold values. Because comparison of digital signals requires relatively little time, it is possible to achieve high processing speeds even with relatively slow digital circuits to permit the economic manufacture of digital eddy-current test instruments.

An apparatus for carrying out the above-mentioned method provides means for moving a coil relatively to test specimens to generate alternating magnetic fields which induce eddy-currents in the respective specimen. The eddy-currents cause a secondary magnetic field in the coil or a sensing coil. The coil is connected to means for evaluating the measured values. These evaluating means include analog/digital converters, a computer, memory for storing imaginary and real parts of digital values and memory containing threshold values.

BRIEF DESCRIPTION OF THE DRAWINGS

Further details, features and advantages of the invention are shown not only in the claims, but also in the following detailed description of the preferred embodiment which is also shown in the accompanying drawings in which:

DETAILED DESCRIPTION OF THE PREFERRED EMBODIMENT

Figure 1B:
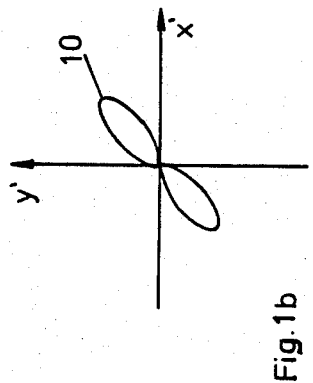
FIGS. 1a to 1d illustrate diagrams of measurement signals shown in the complex plane at various stages of known eddy-current test instrument operation.
Figure 1D:
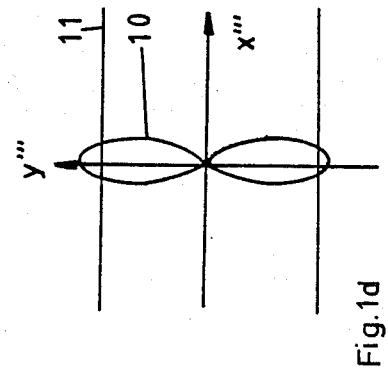
Figure 1A:
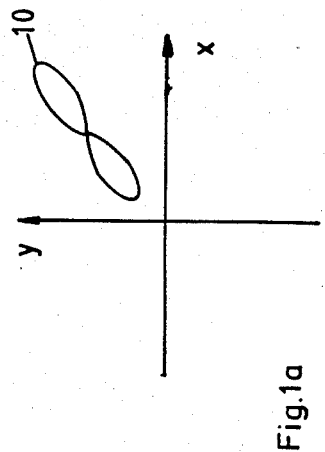
Figure 1C:
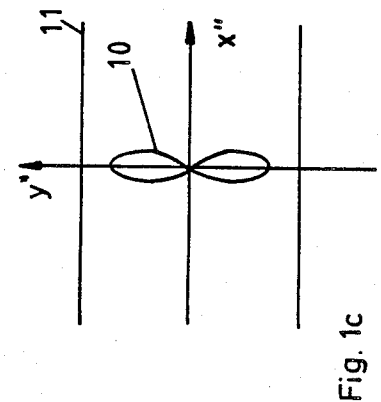

FIGS. 1a to 1d show a known prior art fault indication method. FIG. 1a shows a measurement signal obtained from a relative movement between a test specimen and a sensing coil of a non-adjusted analog eddy-current test instrument in the complex cartesian plane. The measurement signal describes a loop (10) whose size and form indicates faults in the test specimen. Disturbances not caused from faults displace the measurement signal away from the complex plane. To reduce the influence of disturbances, the disturbance signals are eliminated as much as possible by adjustments. After adjustment, the measurement signals have a pattern shown in FIG. 1b, i.e. the loop is displaced towards the origin of the coordinate axes X and Y. Rotating the phase position of loop (10) so that at least one maximum falls in a coordinate axis further reduces the influence of disturbance and results in a measurement signal as shown in FIG. 1c. Compensation and amplification of the rotated measurement signal is then made and results in a measurement signal shown in FIG. 1d. After rotation, compensation and amplification, the measurement signal is compared with a fault threshold (11). If the amplified loop (10) exceeds the fault threshold (11) an indication signal is generated.

Figure 2A:
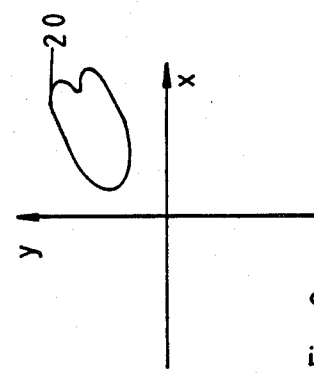
FIGS. 2a to 2e illustrate diagrams of measurement signals and threshold values shown in the complex plane at various stages of eddy-current test instrument operation according to the invention.

In the method according to the invention, fault-free test specimens are first measured using the eddy-current principle and the measured values are converted to digital values. Any disturbance signals present, which relate, for example, to differences in the two branches of the differentially connected coil halves or to lift-off effects, are detected. It is therefore possible to measure all disturbances coming from the test specimen itself or resulting from the guidance and support arrangement of the test specimen or of the coil. The measured values of the test specimen are within an area of some shape. A typical area is shown in FIG. 2a and numbered (20). The measured values containing the detected disturbance signals of the area (20) are stored for further processing to determine compensation values.

To determine the compensation values, the center of gravity of the area (20) is determined, not for the absolute number of measurement values, but for the surface distribution of the values. Each measured value is only used once when determining the center of gravity. The measured values cover an area whose center of gravity is compensated. The result can be a center of gravity value not covered by the measuring equipment and not obtainable with only the measuring equipment. Conventional eddy-current test instruments cannot determine this value because the measured values correspond to points of the surface which are on a grid resulting from the resolution of the digital values boundary points define the area. The points of the grid not occupied by measured values must not be filled to determine the center of gravity. Compensation then follows corresponding to the coordinates of the center of gravity. This displaces the area to a position shown in FIG. 2b to the origin of the X-Y coordinate area of the complex plane. A further processing step now follows whereby the center phase position of the area (20) is determined. The center phase position is obtained by averaging the phase positions of the various points. The area (20) is then rotated by the phase angle of the center phase position into one of the coordinate axis is made. FIG. 2c shows the area (20) rotated by the appropriate phase angle. The purpose of this is to place the main axis of the disturbance signals into the X coordinate axis (or Y coordinate axis) in order to obtain the lowest disturbance signal level on the Y coordinate axis (or X coordinate axis respectively). Accordingly, there is an optimum signal-to-disturbance characteristic in this coordinate axis and the optimum phase position obtained when the lowest disturbance signal levels are present on the selected evaluation axis. The threshold values are then determined. The measurement values defining the boundary of the area (20) are used to obtain a simple geometric envelope. A rectangular envelope (21) is shown in FIG. 2d. The threshold values, by the coordinates of the center of gravity and the angular rotation into the phase position of the area (20), are transformed onto the envelope. The rectangle is a very simple envelope, but more complicated envelopes can be used if the expense is justified.

The threshold values so transformed form the comparative values. FIG. 2e represents the rectangle (21) of the transformed threshold values.

Figure 2B:
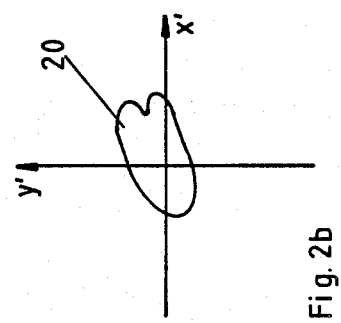
Figure 2C:
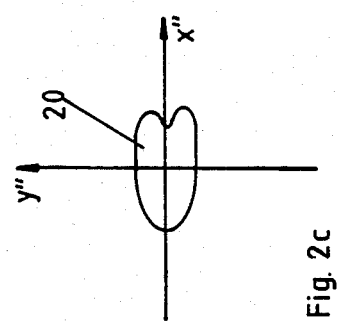
Figure 2D:
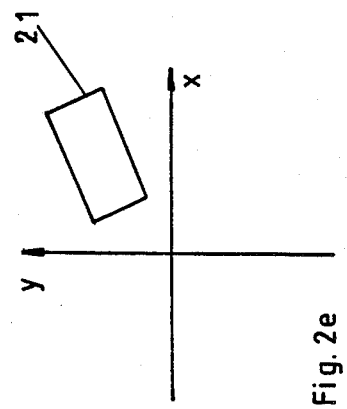
Figure 2E:
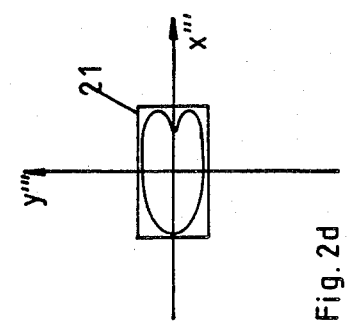

The first compensation step whose result is shown in FIG. 2b includes a displacement of the measurement values to the following relation: $Z-Zo$, with Z designating the positions of the measured values in the complex plane and Zo the position of the center of gravity of the measured values.

If P designates the phase angle of center phase position of the area (20), the phase rotation whose results is shown in FIG. 2c is expressed by the relation $(Z-Zo) e^{jP}$. Once the envelope is determined as shown in FIG. 2d, if So indicates the position of the threshold values resulting from FIG. 2d, then the inverse transformation includes the relation:

$$S = 4(So + Zo) e^{-jP}$$

with S being the position of the transformed threshold values shown in FIG. 2e. Since the measurement values in the above method steps are first converted into digital form and then processed further in the manner stated, control levels, noise and dynamics are of lesser importance compared to analog fault detection.

Figure 3:
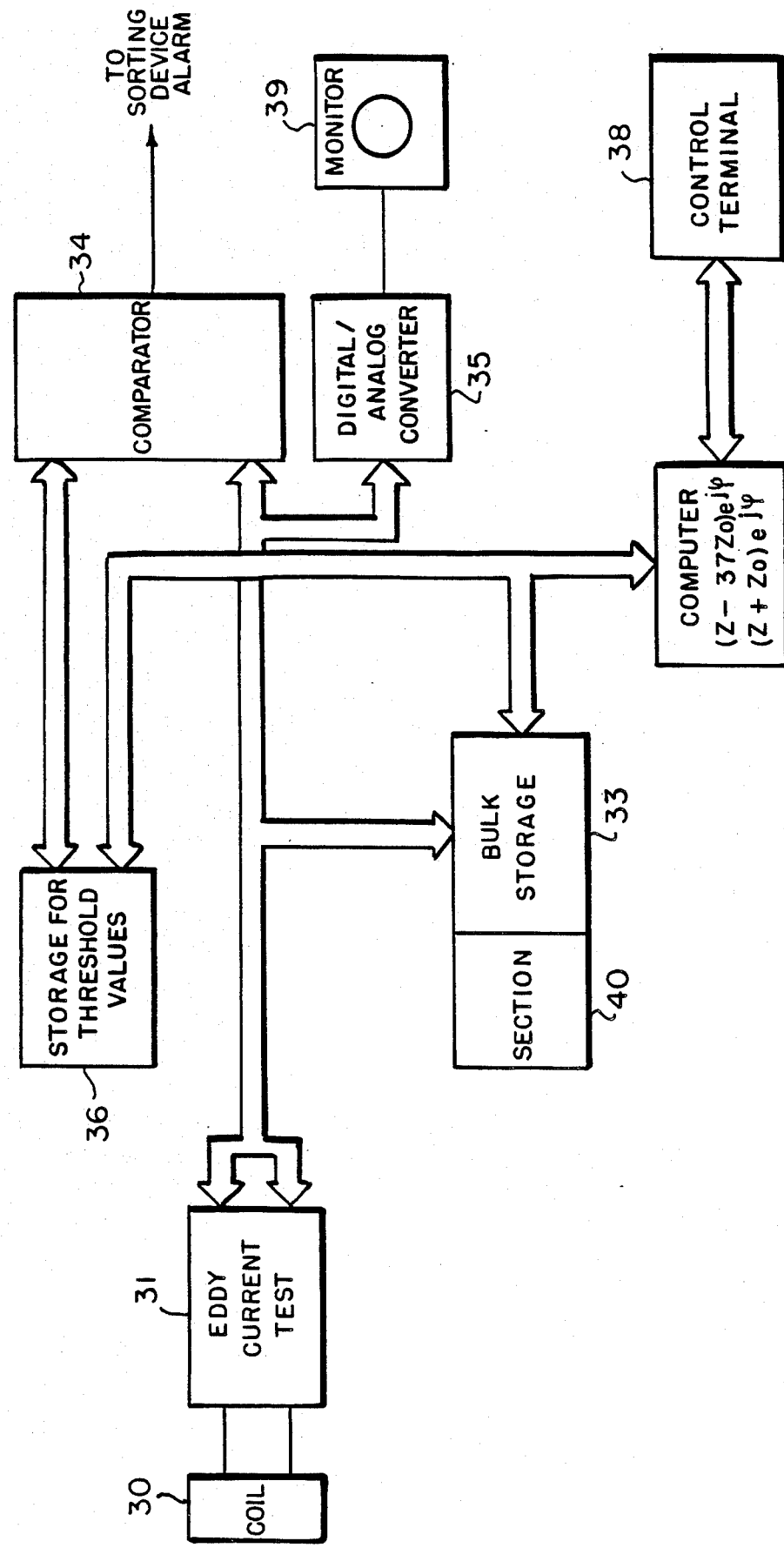
FIG. 3 illustrates a circuit diagram of a device for materials testing in accordance with the eddy-current principle.

As shown in FIG. 3, a device for implementation of the above method contains a coil (30) or a sensing coil. The coil (30) is connected to a coil driver, not illustrated, with which one or various frequencies can be generated one after the other. The coil (30) is connected with a known eddy-current test instrument (31) which carries out an analog/digital conversion of the measured values and provides at its output the real and the imaginary part respectively of the measured values. Eddy-current test instruments of this type are available from NUKEM GmbH, Rodenbacher Chaussee 6, Hanau, as models DOS-01 and AEK-01. The real and imaginary parts of the measured values pass through a bus (32) to a memory (33), the first input of comparators (34), and a digital-analog converter (35). The comparators can be constructed from commercially available logical modules. The outputs of the memory (33) are connected to the inputs of a memory (36) for storing the threshold values and to a computer (37) e.g. a microprocessor. The computer (37) used can be a processor commercially available from the companies Eltec or Force and designated SAC 200 or MC 68000. The threshold values in the memory (36) are fed to the second input of the comparator (34) which emits a signal as an alarm and/or to a sorting device when the threshold values are exceeded, depending on the appropriate mode of operation. The sorting device then picks out the faulty test specimen. The computer (37) is further connected to a control terminal (38). A monitor (39) is connected to the digital-analog converter (35). A section (40) of the memory (33) is reserved for parameters.

The arrangement shown in FIG. 3 works in two operating modes, namely a "learning" mode and a "measuring" mode. These modes are set at the control terminal (38).

In the "learning" mode, fault-free test specimens are measured to determine the area (20) shown in FIG. 2a. The measured values pass to the memory (33). All disturbances occurring during testing are contained in the measurement values. This is a considerable advantage over known eddy-current test instruments. By taking all disturbances into account, it is possible to achieve an optimum setting of the test instrument. It has proved advantageous to use about 10 to 20 test specimens or 10 to 20 m of pipe in the case of tubular test specimens in the "learning" mode. If in the "measuring" mode that follows a number of extreme values are detected, these can be taken into account in a "re-learning phase" in which the points are moved within the area (20), after which a further "learning" mode takes place. The setting of known eddy-current test instruments on the other hand is based on a single test pipe, so that an optimum setting would only be possible by chance, i.e. that the test pipe chances to supply the optimum compensation point or phase position of the disturbance factor.

After completion of measurement of a series of test specimens, the measured values are processed in the manner described above. SAC 200 or MC 68000 processors are so designed that the transformation steps shown in FIGS. 2a to 2c, displayed graphically and numerically one after the other on the monitor (39), controlled by the computer (37). When the measured values with the compensation and phase rotation values has been determined, the threshold values can be placed optimally about this area. Here too there is an advantage over known test instruments: the measurement signal is not amplified so that it exceeds the sorting threshold. Instead, the thresholds adjust to the fault signals. If the measurement signals are not subjected to constant analog amplification, the envelope of the threshold values is thereby adapted to the fault signals. This ensures the greatest possible dynamics.

The threshold values determined are inversely transformed to the value range of the original measured data. The transfer of the threshold values to memory (36) can take place following changeover from the "learning" mode to "measuring" mode.

The electronic measuring system then only has to make the comparison between set point and actual value in the measuring mode, which is possible using normal computers. In test operation, the comparators (34) only check whether the set of values in the threshold value stored in memory (36) is exceeded by the measurement signal. In this event, a sorting or alarm signal is given. The comparators (34) therefore determine whether the measured pair of values consisting of complex numbers is "set" in the threshold value stored in memory (36) or not. Each pair of values consisting of complex numbers represents the coordinates of a grid point in the surface of the measurement values. This surface is designated above as the area (20). Each grid point has a storage cell of the threshold value in memory (36) allocated to it. A pair of values comprising the two complex numbers of a measured value forms a storage address. The contents of the appropriate storage cell indicate whether the measured value is within the area (21) or not. The storage locations each relate to the smallest digital step with which the measured values are resolved. Because of the grid structure with which the respective field is determined, there are no gaps. In the "learning" mode, the computer (37) fills the appropriate values for each grid point into the memory (33). After transformation, the values are available as the threshold values stored in memory (36). If larger gaps are present between the grid points, intermediate values can be obtained by interpolation and input into appropriate storage locations. It has been found that with a test velocity of 6 m/s, the test can proceed at a pulse rate of 5 KHz without temporary difficulties occurring during the comparison and during further processing of the result. The measurement data are fed parallel to the D/A converter (35) that controls the monitor (39). The system is operated using a commercially available terminal (e.g. VT 100 from DEC).

To further simplify setting of the instrument for known test specimens, the memory (33) has reserved a memory portion (40) to file complete sets of parameters (measuring frequency, damping, thresholds etc.) under a keyword. A list with all parameter sets can be called up and selected at the control terminal (38).

I claim:

1. A method for determining faults in an electrically conductive testing material having an unknown fault structure comprising the steps of:
    detecting a plurality of eddy-currents established in a fault-free test specimen;
    converting said plurality of detected eddy-currents into digital values, each digital value representing a complex number in a complex plane;
    determining a threshold envelope corresponding to said digital values, said threshold envelope determining step including the steps of:
    determining an area in said complex plane in which said digital values occur,
    calculating coordinates in said complex plane for a center of gravity corresponding to said digital values,
    calculating a phase angle between one axis of said complex plane and a longitudinal axis of said area,
    displacing said center of gravity to an origin of said complex plane,
    rotating said longitudinal axis by said phase angle toward the one axis of said complex plane,
    generating said threshold envelope which encloses said area, and
    displacing said threshold envelope by said coordinate of said center of gravity and rotating said displaced threshold envelope by said phase angle;

detecting at least one eddy-current established in said testing material;

converting said at least one detected eddy-current into a second digital value; and comparing said second digital value with said threshold envelope to determine if a fault exists in said testing material.

2. A method according to claim 1 wherein said phase angle calculation step calculates said longitudinal axis of said area by calculating a mean value of phase angles for each digital value.

3. A method to claim 1 further including the steps of:
displaying on said monitor said digital values;
displaying on said monitor said digital values after said first displacement step;
displaying on said monitor said digital values after said first rotation step; and
displaying on said monitor said threshold envelope after said threshold envelope determination step.

4. A method according to claim 1 further including the steps of amplifying said plurality of detected eddy-currents.

5. A method according to claim 1 wherein said threshold envelope determining step determines a threshold envelope having a simple geometric form.

6. A method according to claim 5 wherein said step of determining threshold envelope determines a rectangular threshold envelope.

7. A method according to claim which further includes the steps of storing said digital values and storing said threshold values.

8. A method for determining faults in an electrically conductive testing material having an unknown fault structure comprising the steps of:
detecting at least one eddy-current established in said testing material;
converting said at least one detected eddy-current into a digital value representing a complex number; and
comparing said digital value with a predetermined threshold envelope having a rectangular form to determine if said testing material contains a fault, said predetermined threshold envelope representing detected disturbances not due to faults in said testing material.

9. An apparatus for determining faults in an electrically conductive material having an unknown fault structure comprising:
means for detecting eddy-currents induced in said test material;
means for converting said detected eddy-currents into digital values, each digital value representing a complex number in a complex plane;
means for determining a threshold envelope corresponding to said digital values, said threshold envelope determining means including:
means for determining an area in the complex plane in which said digital values occur,
means for calculating coordinates in said complex plane for a center of gravity corresponding to said digital values,
means for calculating a phase angle between one axis of the complex plane and a longitudinal axis of said area,
means for displacing said center of gravity to the origin of the complex plane,
means for rotating said longitudinal axis by said phase angle toward the one axis of the complex plane, and
means for generating said threshold envelope enclosing said area, and displacing said threshold envelope by said coordinate of said center of gravity and rotating said displaced threshold envelope by said phase angle;
means for detecting at least one eddy-current established in said testing material;
means for converting said at least one detected eddy-current into a second digital value; and
means for comparing said digital value with said threshold envelope to determine if a fault exists in said testing material.

10. An apparatus according to claim 9 further including a monitor.

11. An apparatus according to claim 9 further including memory for storing parameters related to said test specimen.

12. An apparatus according to claim 9 further including memory means for storing said digital values and said threshold envelope.

13. An apparatus according to claim 12 wherein said digital values have real and imaginary parts representing an address in said memory means.

* * * * *